(12) United States Patent
Nitzan et al.

(10) Patent No.: US 7,647,100 B2
(45) Date of Patent: Jan. 12, 2010

(54) METHOD, APPARATUS, AND KIT FOR ONYCHOMYCOSIS TREATMENT

(75) Inventors: Zvika Nitzan, Zofit (IL); Dov Tamarkin, Maccabim (IL); Daniela Mavor, Tel Aviv (IL); Nurit Harel, Tel Aviv (IL); Noam Emanuel, Jerusalem (IL)

(73) Assignee: Power Paper Ltd., Beit Shemesh (IL)

( * ) Notice: Subject to any disclaimer, the term of this patent is extended or adjusted under 35 U.S.C. 154(b) by 846 days.

(21) Appl. No.: 10/890,297

(22) Filed: Jul. 14, 2004

(65) Prior Publication Data
US 2005/0038375 A1 Feb. 17, 2005

Related U.S. Application Data

(60) Provisional application No. 60/486,973, filed on Jul. 14, 2003.

(51) Int. Cl.
*A61N 1/30* (2006.01)
(52) U.S. Cl. ........................................................ 604/20
(58) Field of Classification Search .................. 604/20, 604/890.1
See application file for complete search history.

(56) References Cited

U.S. PATENT DOCUMENTS 5,792,097 A * 8/1998 Reddy ........................ 604/20
6,078,842 A 6/2000 Gross et al.
6,157,858 A 12/2000 Gross et al.
6,317,630 B1 11/2001 Gross et al.
6,477,410 B1 * 11/2002 Henley et al. ................. 604/20
2003/0018295 A1 1/2003 Henley et al.
2003/0144625 A1 7/2003 Sherman et al.

FOREIGN PATENT DOCUMENTS

WO WO 03/035167 5/2003
WO WO 03/047503 6/2003

* cited by examiner

*Primary Examiner*—Nicholas D Lucchesi
*Assistant Examiner*—Christopher D Koharski
(74) *Attorney, Agent, or Firm*—Kenyon & Kenyon LLP

(57) ABSTRACT

Methods, apparatus, and kits for onychomycosis treatment are presented. In one embodiment, a kit for treatment includes an anti-fungal agent, in a composition, and an electrically powered patch. Exemplary embodiments of the patch include a first electrode, a power source having a first and second terminal, a second electrode coupled to the second terminal of the power source, and a base member supporting the first electrode, the second electrode, and the power source. Embodiments include those where the first and second electrode and power source are printed on the base member. Anti-fungal agents may be unionized while the composition includes an ionizing agent. Home use may be practiced, as embodiments include those in which the voltage or current of the power source cannot be adjusted by a user. Exemplary methods include the selection of a nail or diseased area to which treatment is desired and administering the kit as described.

40 Claims, 12 Drawing Sheets

METHOD, APPARATUS, AND KIT FOR ONYCHOMYCOSIS TREATMENT

This application claims priority to U.S. Provisional Application Ser. No. 60/486,973, filed Jul. 14, 2003 entitled "Onychomycosis Treatment," the content of which is incorporated herein by reference in its entirety.

BACKGROUND

Onychomycosis is a disease of the nail caused by yeast, dermatophytes, or other molds, and represents approximately 50% of all nail disorders. Toenail infection accounts for approximately 80% of onychomycosis incidence, while fingernails are affected in about 20% of the cases. Dermatophytes are the most frequent cause of nail plate invasion, particularly in toenail onychomycosis. Onychomycosis caused by a dermatophyte is termed tinea unguium. *Trichophyton rubrum* is by far the most frequently isolated dermatophyte, followed by *T. mentagrophytes*. Distal subungual onychomycosis is the most common presentation of tinea unguium, with the main site of entry through the hyponychium (the thickened epidermis underneath the free distal end of a nail) progressing in time to involve the nail bed and the nail plate. Discoloration, onycholysis, and accumulation of subungual debris and nail plate dystrophy characterize the disease. The disease adversely affects the quality of life of its victims, with subject complaints ranging from unsightly nails and discomfort with footwear, to more serious complications including secondary bacterial infections.

Many methods are known for the treatment of fungal infections, including the oral and topical use of antibiotics (e.g., nystatin and amphotericin B), imidazole anti-fungal agents such as miconazole, clotrimazole, fluconazole, econazole and sulconazole, and non-imidazole fungal agents such as the allylamine derivatives terbinafine and naftifine, and the benzylamine butenafine.

However, onychomycosis has proven to be resistant to most treatments. Nail fungal infections reside in an area difficult to access by conventional topical treatment and anti-fungal drugs cannot readily penetrate the nail plate to reach the infection sites under the nail. Therefore, onychomycosis has traditionally been treated by oral administration of anti-fungal drugs; however, clearly this is undesirable due to the potential for side effects of such drugs, in particular those caused by the more potent anti-fungal drugs such as itraconazole and ketoconazole. An alternative method of treatment of onychomycosis is by removal of the nail before treating with a topically active anti-fungal agent; such a method of treatment is equally undesirable. Systemic antimycotic agents require prolonged use and have the potential for significant side effects. Topical agents have usually been of little benefit, primarily because of poor penetration of the anti-fungal agents into and through the nail mass.

Iontophoresis has been known for many years, as a means to deliver drugs and cosmetic active agents into the skin for therapeutic purposes. It is based on mechanisms, which include (a) iontophoresis, in which a charged ion is repelled from an electrode of the same charge, and (b) electroosmosis, based on the convective movement of solvent that occurs through a charged "pore" in response to the preferential passage of counter-ions when an electric field is applied. While widely used in dermal delivery of active agents, iontophoresis has not been utilized hitherto in the treatment of nail infections. Furthermore, the literature is devoid of pragmatic ways to enable a system, which is practically and conveniently usable for long periods of daily treatment.

In the context of the present invention, the term "iontophoresis" will stand for any method of electrical dermal delivery of substances, including electrotransportation, iontophoresis, electroosmosis, electroporation, and/or a combination thereof. The terms "device," "iontophoretic device," "iontophoretic patch," "electrically operated device," and "electrically operated patch," as used herein, will interchangeably stand for any method or device, used for electrical delivery of substances, including electrotransportation, iontophoresis, electroosmosis, and electroporation.

It would therefore be advantageous to have a therapeutic system, based on topical application of a formulation that is capable of penetrating the nail barrier and effectively treating nail fungal diseases, thus avoiding oral administration of anti-fungal drugs and the necessity of removing the nail.

BRIEF DESCRIPTION OF THE DRAWINGS

The various features of the invention will best be appreciated by simultaneous reference to the description which follows and the accompanying drawings, wherein like numerals indicate like elements, and in which.

DESCRIPTION

Embodiments of the present invention are useful for topically treating onychomycosis, i.e., a disease (e.g., a fungal infection) of the nail plate on the hands or feet. Nail fungal disease is usually caused by *Epidermophyton, Microsporum*, and/or *Trichophyton* and produces nails that are opaque, white, thickened, friable, and brittle. As used herein, reference to a "nail" includes reference to one, or some, or all parts of the nail, including the nail plate (the stratum corneum unguis, which is the horny compact outer layer of the nail, i.e., visible part of the nail), the nail bed (the modified area of the epidermis beneath the nail plate, over which the nail plate slides as it grows), the cuticle (the tissue that overlaps the nail plate and rims the base of the nail), the nail folds (the skin folds that frame and support the nail on three sides), the lunula (the whitish half-moon at the base of the nail), the matrix (the hidden part of the nail under the cuticle), and the hyponychium (the thickened epidermis underneath the free distal end of a nail). Nails grow from the matrix. Nails are composed largely of keratin, a hardened protein (that is also in skin and hair). As new cells grow in the matrix, the older cells are pushed out, compacted and take on the familiar flattened, hardened form of a fingernail or toenail.

In accordance with an embodiment of the invention, a device promotes a delivery of a compound from a composition to and through the nail plate and to the nail bed. In an embodiment, the compound is an anti-fungal agent. In an alternate embodiment, the anti-fungal agent is preferably concurrently delivered to at least one of the cuticle, the nail folds, the lunula, the matrix, and the hyponychium.

Embodiments of the invention may have several aspects. One aspect is an electrically operated device, intended for application on the nail. The device may be an iontophoretic device. Another aspect is a composition, comprising an anti-fungal agent and excipients, as suitable to facilitate iontophoretic delivery of the anti-fungal agent into and through the nail plate. A further aspect is a kit comprising an electrically operated device and a composition, comprising an anti-fungal agent. Still, another aspect is the use of the electrically operated device, in combination with the composition to treat onychomycosis.

The Device

The terms "device," "iontophoretic device," "iontophoretic patch," "electrically operated device," and "electrically operated patch," as used herein, will interchangeably stand for any method or device used for electrical delivery of substances, including electrotransportation, iontophoresis, electroosmosis, electroporation, and/or a combination thereof. In a preferred embodiment, the device is a fully or partially printed device, wherein at least one of, or a combination of, or all of, the electrodes, power source, and conductive connections are disposed on a base layer using a suitable printing technique.

Figure 1:
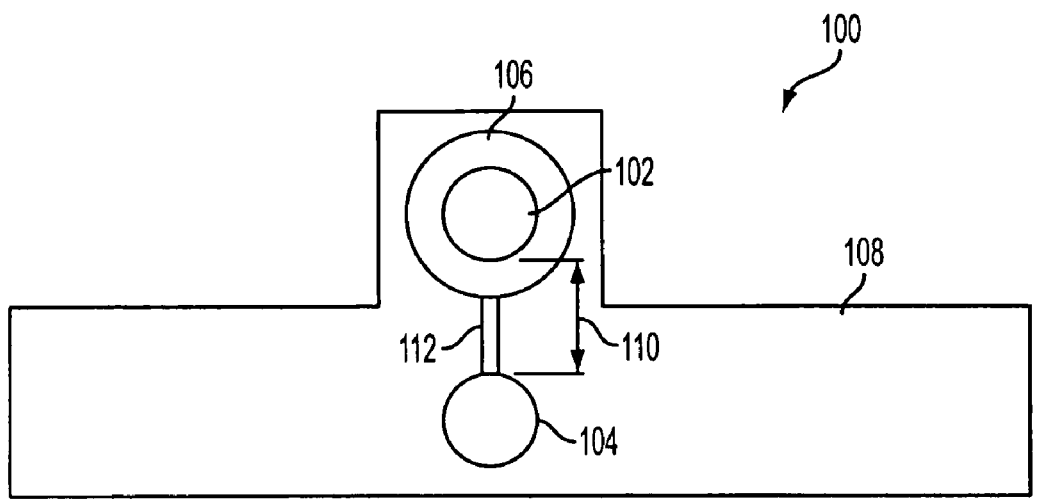
FIG. 1 illustrates a plan view of a device according to one embodiment of the invention.

FIG. 1 illustrates a plan view of a device 100 according to one embodiment of the invention. The device 100 comprises a flexible, wearable patch that can conform to a nail surface and portion of a digit (i.e., finger or toe) or digits of a person. The device may be sized so as to be applied to one digit, or it may be sized so as to be applied to a plurality of digits, such as by wrapping the device around two digits that are next to one another. The device 100 is preferably fabricated from thin and flexible materials, which enable at least those surfaces that contact a patients nail or skin to conform to the contours of the patient when the device 100 is applied thereon. The patch 100 may be provided with an adhesive that may allow the patch 100 to adhere to the nail surface and or surrounding tissue of the nail (not shown). The patch 100 includes a first electrode 102 and a second electrode 104. The patch 100 may also include a power source 106 having a first terminal and a second terminal. As illustrated in the embodiment of FIG. 1, the power source 106 may be coupled to an electrode of the patch 100; in the embodiment of FIG. 1 the power source 106 is coupled to the first electrode 102. The power source 106 may be disposed near to the electrode 102, 104; in another embodiment, however, the power source is positioned as close as possible to the first electrode 102 and may be an integral part of that first electrode 102. In the embodiment of FIG. 1, the power source 106 is disposed beneath the first electrode 102. The patch 100 further includes a base member 108, which supports the first electrode 102, second electrode 104, and power source 106, and maintains the first electrode 102 and second electrode 104 in a spaced-relation to each other to define a gap 110 therebetween. In one embodiment, the gap 110 may include a range that is greater than about 5 to about 10 mm; the gap size will depend, at least in part, on the size of the device. It will be noted that the minimum range of 5 to 10 mm is derived from a related embodiment, wherein the generation of an oxidizing agent, such as zinc, is desired. It is noted, however that the configuration for generation of an oxidizing agent may be different than a configuration for treatment of onychomycosis. A conductor 112 couples the second electrode 104 to the first terminal of the power source 106. In an embodiment having two patch electrodes, they may be connected to the power source using conventional conductive wire. Conventional conductive wire may also be used in a single patch embodiment. In an alternate embodiment, the conductor 112 may lie on a distal side (or alternatively within) the base member 108. Base member 108 may be built up of multiple layers to facilitate the embedding of a conductor within the electrically insulative material of a base member. Examples of conductors that may couple the electrodes to the power source include, but are not limited to wiring (flat or round), conductive ink, conductive adhesive, printed connection means, soldered connection means, connection means attached by UV, glued connection means, conductive EVA welding, and a combination thereof. While the embodiment of FIG. 1 illustrates circular electrodes and a circular power source, other shapes of electrodes and power sources may be used without departing from the scope of the invention. Furthermore, FIG. 1 illustrates only one possible arrangement of electrodes and battery on a base member, other arrangements, such as, but not limited to, those illustrated in FIGS. 5-9 may be used without departing from the scope of the invention.

Base member 108 may be manufactured from any suitable material, which can accommodate the anti-fungal agent delivery patch components. Suitable materials include, but are not limited to woven material, non-woven material, polymers, conducting material, non-conducting material, paper, cardboard, plastic, synthetic materials, natural materials, fabric, metals, wood, glass, Perspex, or a combination thereof. Preferably, the material of base member 108 is a non-conductive material. More preferably, base member 108 is made from polyester. Optionally, base member 108 can be made up of a plurality of materials, which can be stacked or connected in a co-planar way by any suitable attachment means. Preferably, base member 108 is made up of one continuous piece of material.

According to a preferred embodiment of the present invention, the power source 106 may be an electrochemical cell. In a preferred embodiment, the power source may be thin and flexible. In one embodiment, the power source 106 may be disposable. In one embodiment, the power source 106 may be rechargeable. While the first electrode 102 may be identified as an anode and the second electrode 104 may be identified as a cathode, those of skill will recognize that these designations may be reversed.

Figure 2:
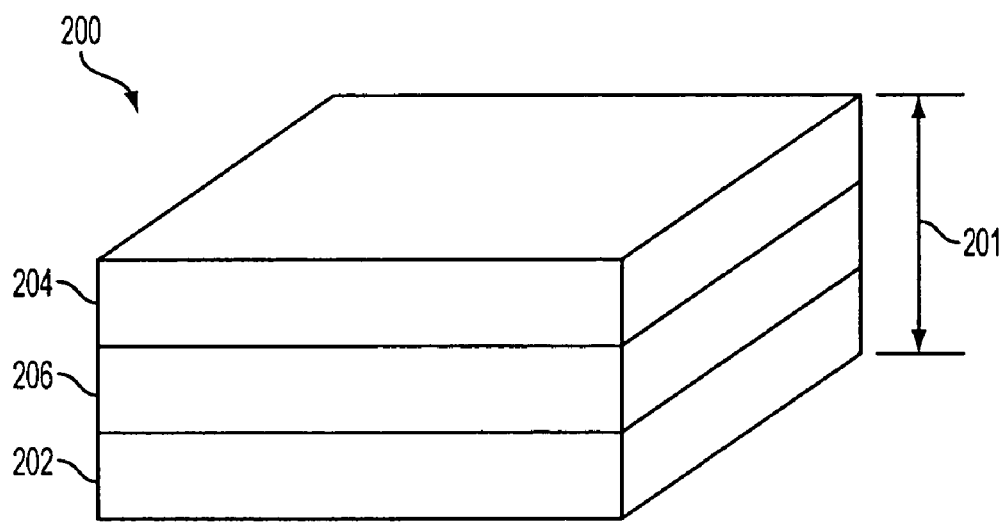
FIG. 2 illustrates a schematic representation of an exemplary power source in accordance with an embodiment of the invention.

FIG. 2 illustrates a schematic representation of an exemplary power source 200 in accordance with an embodiment of the invention. Preferably, power source 200 is thin and flexible. The term "power source" as used herein includes, but is not limited to, any suitable cell in which chemical energy is converted to electric energy by a spontaneous electron transfer reaction. The term includes cells with non-spontaneous reactions, cells with spontaneous reactions, galvanic cells, electrolytic cells, and/or a combination thereof. In the embodiment of FIG. 2, the power source is depicted as an electrochemical cell 200. The thickness 201 of the electrochemical cell 200 may be up to 4 mm, more preferably up to 2 mm and most preferably up to 1 mm. In a presently preferred embodiment, electrochemical cell 200 includes a positive pole layer 202, a negative pole layer 204, and an electrolyte layer 206 interposed therebetween. By way of example, a suitable electrochemical cell 200 is described in U.S. Pat. Nos. 5,652,043, 5,897,522, and 5,811,204, each of which are incorporated herein by reference in their entireties. Briefly, the electrochemical cell described in the above-identified U.S. patents is an open liquid state, electrochemical cell, which can be used as a primary or rechargeable power source for various miniaturized and portable electrically powered devices of compact design. In one embodiment, a preferable electrochemical cell 200 may comprise a first layer of insoluble negative pole 204, a second layer of insoluble positive pole 202, and a third layer of aqueous electrolyte 206 disposed between the first 204 and second 202 layers and may include (a) a deliquescent material (not shown) for keeping the open cell wet at all times; (b) an electroactive soluble material (not shown) for obtaining required ionic conductivity; and, (c) a water-soluble polymer (not shown) for obtaining a required viscosity for adhering the first and second layers to the third layer.

Yet, in another preferred embodiment, an electrochemical cell may comprise a plurality of self-contained, serially connected galvanic power sources, as described for example in U.S. Pat. No. 6,421,561, which is incorporated herein by reference in its entirety. Several preferred embodiments of the disclosed electrochemical cell include (i) engaging the electrolyte layer in a porous substance, such as, but not limited to, a filter paper, a plastic membrane, a cellulose membrane and a cloth; (ii) having the first layer of insoluble positive pole include manganese-dioxide powder and the second layer of insoluble negative pole include zinc powder; (iii) having the first layer of insoluble negative pole and/or the second layer of insoluble positive pole further include carbon powder; (iv) selecting the electroactive soluble from zinc-chloride, zinc-bromide, zinc-fluoride and potassium-hydroxide; (v) having the first layer of insoluble negative pole include silver-oxide powder and the second layer of insoluble positive pole include zinc powder and the electroactive soluble material is potassium-hydroxide; (vi) having the first layer of insoluble negative pole include cadmium powder and the second layer of insoluble positive pole include nickel-oxide powder and selecting the electroactive soluble material to be potassium-hydroxide; (vii) having the first layer of insoluble negative pole include iron powder and the second layer of insoluble positive pole include nickel-oxide powder and selecting the electroactive soluble material to be potassium-hydroxide; (viii) having the first layer of insoluble negative pole and the second layer, of insoluble positive pole include lead-oxide powder, then cell is charged by voltage applied to the poles and the electroactive soluble material is selected in this case to be sulfuric-acid; (ix) the deliquescent material and the electroactive soluble material can, be the same material such as zinc-chloride, zinc-bromide, zinc-fluoride and potassium-hydroxide; (x) the deliquescent material is selected from the group consisting of calcium-bromide, potassium-biphosphate and potassium-acetate; (xi) the water-soluble polymer can be polyvinyl alcohol, polyacrylamide, polyacrylic acid, polyvinylpyrolidone, polyethylenoxide, agar, agarose, starch, hydroxycthylcellulose and combinations and copolymers thereof; (xii) the water-soluble polymer and the deliquescent material can be the same material such as dextrane, dextranesulfate and combinations and copolymer thereof. An electrochemical cell may preferably incorporate any one or more of the embodiments described above. Preferred configurations for electrochemical cells according to the present invention involve those combinations which are devoid of poisonous compounds.

Preferably, the power source is applied using a suitable printing technique.

A preferred power source, such as power source 106, FIG. 1, provides a direct current electrical potential (voltage) in the range between about 0.5V and about 12V. Such electrical potential can be supplied by a single electrochemical cell or a number of electrochemical cells, linked together, to afford the desirable voltage. For home-use, it may be advantageous to fix the current and/or voltage. Accordingly, in on embodiment, the current and or voltage supplied by a power source is fixed and cannot be adjusted by a user; where a user may include the patient or subject of an Onychomycosis treatment. In yet another embodiment, the electrical potential may be adjusted, to satisfy at least one of the following criteria:

The voltage may be adjusted to enable an iontophoretic delivery of an active agent into and through the nail. For that purpose, voltage may be adjusted to provide an electrical current of between about 0.002 mA/cm$^2$ and 10 mA/cm$^2$.

The voltage may be adjusted to minimize irritation, which may result from excessive electrical current, passing into and through the nail and/or skin. Thus, in a preferred embodiment, the voltage may be adjustable and may be adjusted within a range between about 0.5V and about 12V; and in a more preferred embodiment, the voltage may be adjustable and may be adjusted within a range between about 1V and about 4.5V. In a preferred embodiment, any adjustment may be made through automatic mechanisms, such as sensors.

Optionally, power source may be a single electrochemical cell. However, power source need not be limited to one cell, but may include a plurality of connected electrochemical cells, a plurality of batteries, and/or electronics configured to increase, control, and change phase of the supplied electric current and wherein the power supply is thin and flexible. Electrochemical cell 106 in patch 100 preferably provides electrical potential (voltage) to the desired body area of the subject.

The power supply may optionally be located in any suitable position on the patch.

A power supply to the patch may provide a duty cycle and pulse partition rate of between about 1% and about 99%. The frequency of the power supply may preferably be from about 1 Hz to about 1000 Hz. The power supply may provide voltage in a range of from about 0.2V to about 100V to the patch.

In one preferred embodiment, devices described herein are useful for administering anti-fungal-agents and the like in non-clinical settings, such as the home. Furthermore, in one preferred embodiment, devices described herein utilize one preset voltage and/or current and as such, a user (i.e., the patient) need not adjust the voltage or current of the device.

Returning now to FIG. 1, electrodes may be formed of a metal, e.g., a metal foil or metal deposited or painted on a suitable backing. Electrodes may be applied to the patch by, for example, a suitable printing technology such as, but not limited to, silk print, offset print, jet printing, lamination, materials evaporation or powder dispersion. In one embodiment, at least one of the electrodes 102, 104 comprises silver metal. In a further preferred embodiment, at least one electrode 102, 104 comprises both silver and silver chloride. Yet, in another preferred embodiment, at least one of the electrodes 102, 104 comprises carbon or graphite. In yet another preferred embodiment, at least one of the electrodes 102, 104 comprises zinc. Other examples of suitable metals for electrodes include copper, manganese dioxide, aluminum, platinum, stainless steel, gold, titanium, or a combination thereof. Alternatively, electrodes may be formed of a hydrophobic polymer matrix containing a conductive filler such as a metal powder/flakes, powdered graphite, carbon fibers, or other known electrically conductive filler material. Any other conductive element or compound, including metal and non-metal materials, can be incorporated into the material of the electrodes 102, 104. In an embodiment, the electrodes 102, 104 may be provided as thin sheets coupled to the power source 106, or may be printed onto the base member 108 in spaced relation to each other to define the gap 110 therebetween. Preferably, at least one electrode is an active electrode and at least one electrode is a counter electrode. Optionally, the active electrode can be the cathode or anode or both the cathode and the anode. Defining which electrode is the active electrode is dependent on the charge of the composition (e.g., formulation or anti-fungal agent) being used. Optionally, the electrode area can be continuous, or formed in any shape or configuration. Optionally, each electrode may not have the same shape and/or same area. Optionally, electrodes may be in any suitable conformation in relation to each other including but not limited to a coplanar and cofacial arrangement. Optionally, patch can include a plurality of electrodes, comprised of equal or unequal numbers of anodes and cathodes. Such a multi-electrode patch facilitates providing simultaneously a plurality of treatments with one composition or a plurality of compositions in different body areas or the same body area. Preferably, the active electrode will be disposed on the region of infection and the counter electrode will be disposed on a non-infected region of the digit.

Figure 3:
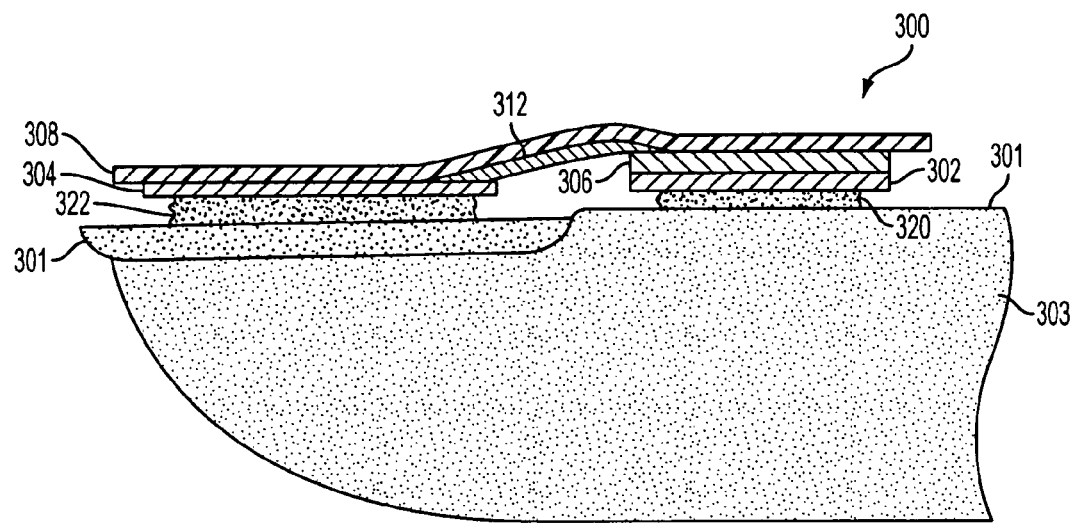
FIG. 3 is a cross-section view of a patch is in contact with the skin and/or nail of a human subject, according to one embodiment of the invention.

FIG. 3 is a cross-section view of a patch 300 that is in contact with the skin and/or nail 301 of a human subject, according to one embodiment of the invention. The figure includes a stylized cross sectional view of a digit (finger or toe) 303, for reference. The figure is not drawn to scale. In the simplified view of FIG. 3, the patch 300 may be comprised of first electrode 302, second electrode 304, power source 306, base member 308, and conductor 312. A first and second interfacing layer 320, 322, each comprised of interfacing material, may be disposed between the patch 300 and the skin and/or nail 301. In the embodiment of FIG. 3, the first interfacing layer 320 is disposed between the first electrode 320 and the nail 301, while second interfacing layer 322 is disposed between the second electrode 304 and the skin 301. The interfacing material may be a conductive material. Without derogating from the generality of optional interfacing materials, one example of an interfacing material may be a conductive hydrogel. It is noted that nothing herein is meant to restrict an interfacing layer from placement on an area comprising both skin and nail, such as on a margin of the nail, e.g., a placement straddling the lunula. In one embodiment, the first electrode and second electrode may be separated by at least a gap, such as gap 110 of FIG. 1 to promote a transdermal treatment of a patient.

Any sequence of application of an anti-fungal agent and an iontophoretic patch is possible according to the present invention, including, but not limited to the following options: (1) The composition, comprising an anti-fungal agent may be added to the patch prior to application, and the patch may then be applied onto the nail; or (2) The composition, comprising an anti-fungal agent may include a conductive hydrogel, which can be attached to the patch or first attached to the nail, followed by patch application onto the nail; or (3) The composition, comprising an anti-fungal agent may be topically applied onto the nail followed by application of the patch; or (4) The composition, comprising an anti-fungal agent may be incorporated into a separate component, which may be coupled to the patch. The patch and separate component may then be applied onto the nail. The separate component may be referred to herein as a retainer. The retainer may be, for example, a pad or other structure having a capacity to store a quantity of composition. A pad may preferably be made up from, for example, a non-woven substance, a mixture of viscose and PET, polypropylene, sponge and a polymeric absorbent substrate (Hydrogel). The retainer may be absorbent and porous. The retainer may alternatively take the form of, for example, a vessel, tube, jar, container, dispenser, or ampoule. It will be appreciated that the present invention contemplates all such retainers as well as others in any shape, size or configuration that serve to retain the conductive fluid and dispense it for use as needed on either the electrodes or upon the skin of a subject. The composition, may include a conductive fluid. The combination of a patch and a retainer may form a kit that may optionally be retained by a patient for use for a variety of applications.

The formation of such conductive fluid will generally be "pharmaceutically acceptable" or "physiologically acceptable" formulations for cosmetic or therapeutic use. As used herein, the terms "pharmaceutically acceptable" and "physiologically acceptably" refer to substances that can be administered to a subject, preferably without excessive adverse side effects (e.g., for a topically applied formulation, skin rash, irritation, etc.). Particular formulations include aqueous gels, cream, pastes, lotions, suspensions, emulsions and solutions or other liquid formulations suitable for topical application known in the art.

In a presently preferred embodiment, the conductive fluid may be an electrically conductive and adhesive hydrogel, suitable for use as a skin contact adhesive and, particularly, suitable for use as an electrical interface for electrodes of medical devices. The hydrogels are cationic acrylates and may be, for example, preferably made from acrylic esters of quaternary chlorides and/or sulfates or acrylic amides of quaternary chlorides. They can be formed by free radical polymerization in the presence of water, preferably by ultra-violet curing with initiator and multi-functional cross-linking agent. The hydrogel may preferably include a buffer system to help prevent discoloration of the hydrogels and/or hydrolysis of the hydrogels and/or to improve shelf-life.

Other additives may be incorporated into the present hydrogels either before or after curing (e.g., conductivity enhancers, pharmaceuticals, humectant plasticizers, etc.) depending on intended end-use. An additive that is preferably added to the hydrogel is a conductive adhesive matter (additive) that serves to allow the conductive fluid to both attach patch to the skin of the subject and to serve as the conductive interface between the electrode and the skin. The adhesive additive is preferably a polymeric adhesive and may be pressure or temperature activatable or it may be activated by the exposure to the ambient atmosphere.

The preferred hydrogel is sufficiently cohesive, yet remains readily separable. Further details pertaining to hydrogels suitable for use in the context of the present invention are described in, for example, U.S. Pat. No. 5,800,685, which is incorporated herein by reference in its entirety.

In any case, an aqueous conductive fluid in accordance with the teachings of the present invention will typically include water, alcoholic/aqueous solutions, at least one salt or any other charged agent and preferably a buffering medium.

It is appreciated that non-aqueous conductive fluids may also be employed.

Figure 4:
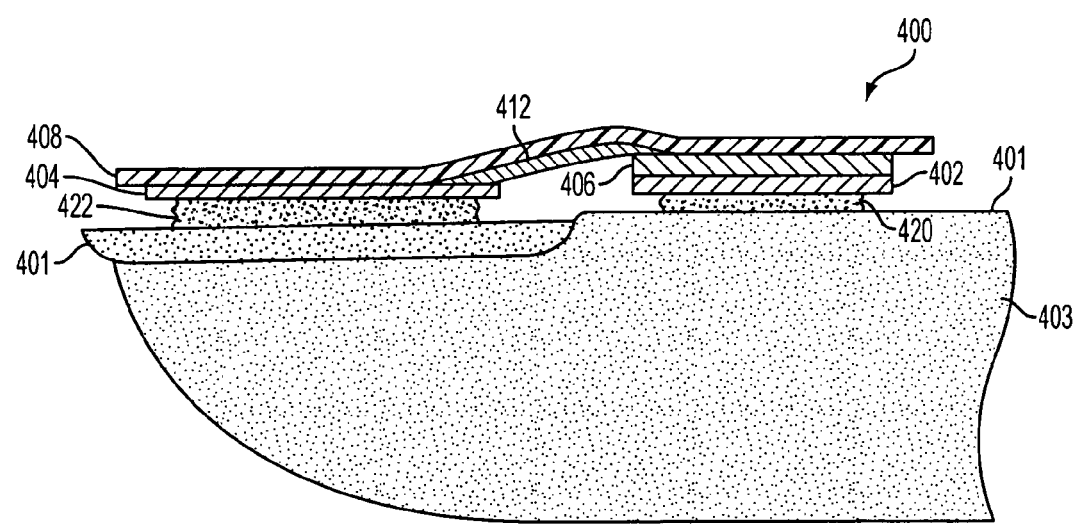
FIG. 4 is a cross-section view of a patch that is in contact with the skin and/or nail of a human subject, according to one embodiment of the invention.

FIG. 4 is a cross-section view of a patch 400 that is in contact with the skin and/or nail 401 of a human subject, according to one embodiment of the invention. The figure includes a stylized cross sectional view of a digit (finger or toe) 403, for reference. The figure is not drawn to scale. In the simplified view of FIG. 4, the patch 400 may be comprised of first electrode 402, second electrode 404, power source 406, base member 408, and conductor 412. A first and second retainer 420, 422 may each include a porous and/or absorbent material for retaining a formulation. The formulation may comprise an anti-fungal agent. The first and second substrates may be interposed between the patch 400 and the skin and/or nail 401. Upon completion of a circuit formed by the series path of the first electrode 402, power source 406, conductor 412, second electrode 404, and skin and or nail 401 and application of current through the series path, the patch 400 can deliver a quantity of an active ingredient, such as anti-fungal agent, to the subject's nail plate, nail bed, skin, and any surrounding area.

Optionally, anti-fungal agents according to the present invention may be part of a formulation, placed in the interface area between one or both of the electrodes of the device. Providing that they possess a certain degree of water solubility, they can be mobilized from the formulation towards the body surface, via the electromotive forces of iontophoresis and/or electro-osmosis. The term 'formulation' as used herein includes any type of suitable formulation, which can accommodate an anti-fungal agent. The term includes conductive layers, such as aqueous gel or hydrogel. The term further includes any pharmaceutical or cosmetic active or inactive formulation, including active ingredients, solvents, fragrance and additives. Additives to such formulations include but are not limited to water, surfactants, emulsifiers, diglycerides, triglycerides, stabilizing agents, thickening agents, alpha-hydroxy carboxylic acids, antioxidants, preservatives, moisturizers, petroleum, mineral oil, glycerol, ethanol, propanol, isopropanol, butanol, polymeric gelling agents, flavoring, colorant and odorant agents and other formulation components, used in the art of pharmaceutical and cosmetic formulary. In an embodiment, wherein the anti-fungal agent is placed in the interface area between one or both of the electrodes, the formulation containing the anti-fungal agent can optionally be applied directly onto the skin, or alternatively the anti-fungal agent is disposed in a retainer component, such as, but not limited to a sponge or hydrogel. Preferably, the formulation is contained in a conductive layer, such as, but not limited to, a hydrogel. In such an embodiment, the device of the present invention preferably facilitates surface treatment of the nail and/or surrounding areas. Optionally, such an embodiment can result in a combination of transdermal delivery of the anti-fungal agent and surface treatment with the anti-fungal agent.

In order to facilitate use, a device in accordance with an embodiment of the invention is preferably designed to suit the shape and contour of the nails of the hands and feet. FIGS. 5-9 illustrate exemplary embodiments of devices in accordance with the invention. Exemplary embodiments may include circular designs, ring designs, clip designs, thimble designs, designs that wrap the whole finger, glove finger designs, designs may be linear and may be closed using an adhesive tape or hook and loop attachment (e.g., Velcro®). Any other design which provides a thin and flexible device that suits the contour of the finger or toe are acceptable.

Figure 5A:
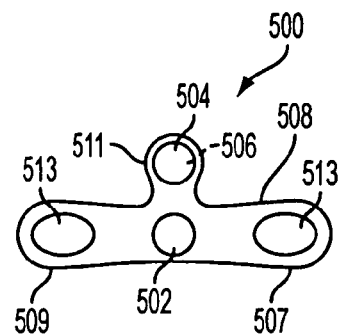
FIGS. 5A, 5B, and 5C illustrate an exemplary embodiment of a device in accordance with the invention.
Figure 5B:
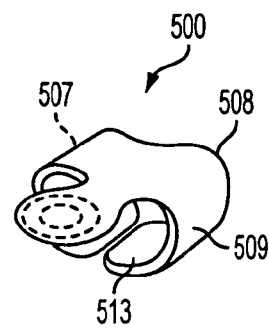
Figure 5C:
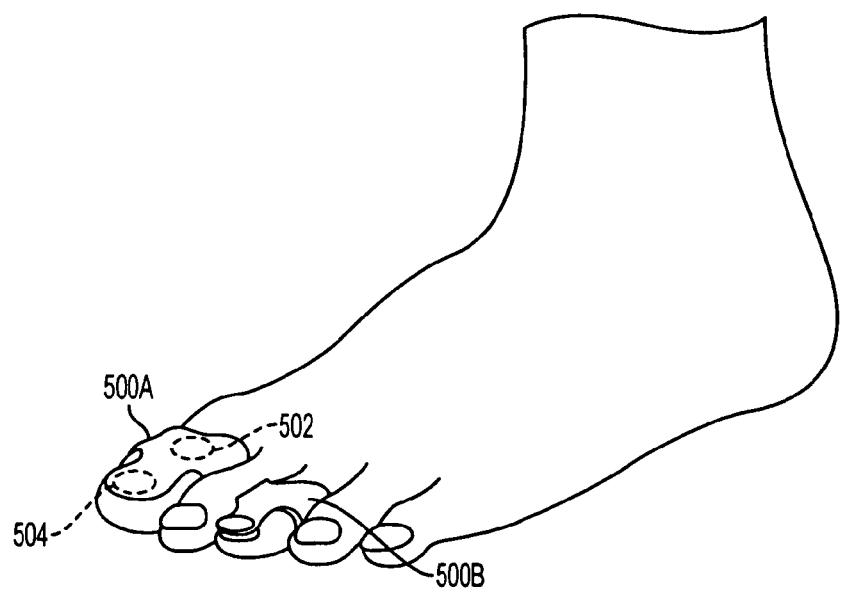

FIG. 5 illustrates an exemplary embodiment of a device in accordance with the invention. In the embodiment of FIG. 5A, a patch 500 comprises a base member 508 having a right lateral portion 507, a left lateral portion 509, and a midline portion 511. An adhesive 513 suitable for attaching the base member 508 to the skin of a patient may be deposited on either or both of the right lateral and left lateral portions 507, 509. A first electrode 502 may be positioned substantially midway between the left and right lateral portions 507, 509. A second electrode 504 may be positioned along the midline portion. The midline portion in the embodiment of FIG. 5 projects, in only one direction, from an imaginary line joining the left and right portions 507, 509. The midline portion being that portion that extends along an imaginary line that is perpendicular to and substantially centered along the imaginary line joining the left and right lateral portions 507, 509. A power source 506 may be interposed between the second electrode 504 and the base member 508. In alternate embodiments, the power source 506 may be placed at any location on the base member 508. FIG. 5B illustrates a configuration of the base member 508 suitable for use on a digit of a patient. In the illustration of FIG. 5B the left and right lateral portions 507, 509 are curvilinearly folded into a ring conformation. The ring conformation is suitable for use on any digit because the left and right folded lateral portions 507, 509 together surround or substantially surround and embrace the digit while the adhesive 513 thereon substantially anchors the base member 508 in place. Iontophoretic treatment, as described herein, may be pragmatically effected on portions of the digit by use of the patch 500. FIG. 5C illustrates two patches 500A and 500B embracing two separate digits of a patient. In the embodiment of FIG. 5C, a first patch 500A encircles a big toe of the patient. A second patch 500B encircles a middle toe of the patient. As schematically illustrated in FIG. 5C, patches of the same conformation may be supplied in different sizes to suit different sizes of digits. As illustrated in FIG. 5C, in a preferred embodiment, an electrode, referred to herein as an active electrode 504, may be disposed on the digit on an infected region and the other electrode, alternatively referred to herein as a counter electrode 502, may be disposed on the digit on a non-infected region.

Figure 6A:
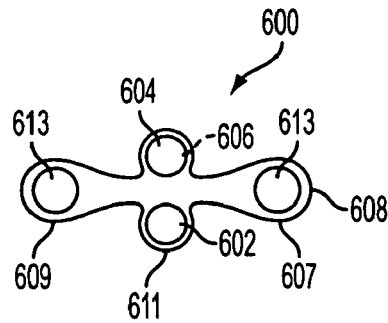
FIGS. 6A, 6B, and 6C illustrate an exemplary embodiment of a device in accordance with the invention.
Figure 6B:
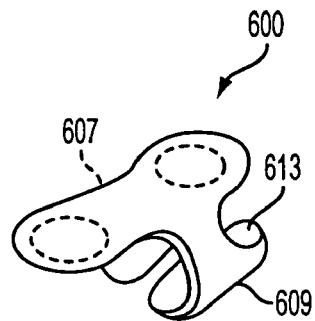

FIG. 6 illustrates an exemplary embodiment of a device in accordance with the invention. In the embodiment of FIG. 6A, a patch 600 comprises a base member 608 having a right lateral portion 607, a left lateral portion 609, and a midline portion 611. An adhesive 613 suitable for attaching the base member 608 to the skin of a patient may be deposited on either or both of the right lateral and left lateral portions 607, 609. The midline portion 611, in the embodiment of FIG. 6, projects in both directions from an imaginary line joining the left and right portions 607, 609. The midline portion 611 being that portion that extends in both directions along an imaginary line that is perpendicular to and substantially centered along the imaginary line joining the left and right lateral portions 607, 609. A first electrode 602 may be positioned on a proximal portion of the midline portion 611. A second electrode 604 may be positioned on a distal portion of the midline portion 611. A power source 606 may be interposed between the second electrode 604 and the base member 608. In alternate embodiments, the power source 606 may be placed at any location on the base member 608. FIG. 6B illustrates a configuration of the base member 608 suitable for use on a digit of a patient. In the illustration of FIG. 6B the left and right lateral portions 607, 609 are curvilinearly folded into a ring conformation. The ring conformation is suitable for use on any digit because the left and right folded lateral portions 607, 609 together surround or substantially surround and embrace the digit while the adhesive 613 thereon substantially anchors the base member 608 in place. Iontophoretic treatment, as described herein, may be pragmatically effected on portions of the digit by use of the patch 600. FIG.

Figure 6C:
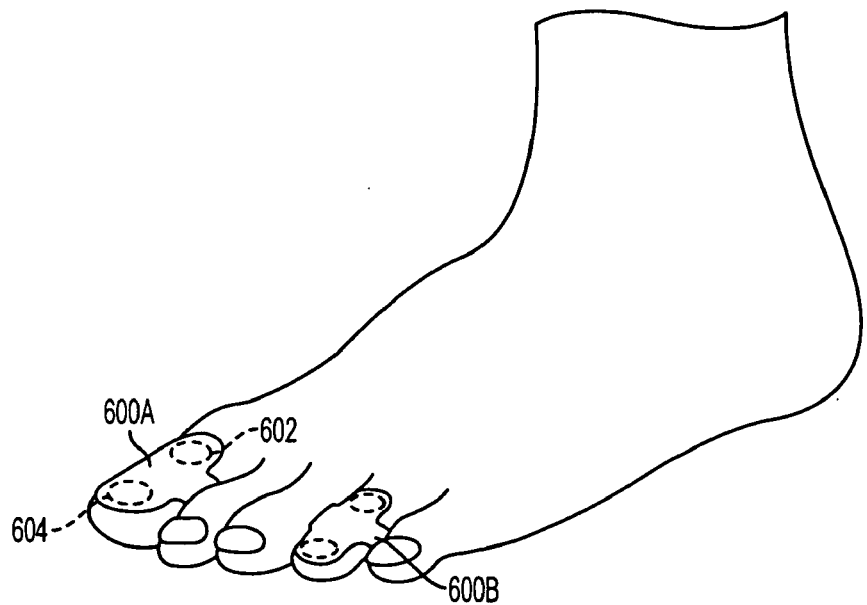

6C illustrates two patches 600A and 600B embracing two separate digits of a patient. In the embodiment of FIG. 6C, a first patch 600A encircles a big toe of the patient. A second patch 600B encircles a fourth toe of the patient. As schematically illustrated in FIG. 6C, patches of the same conformation may be supplied in different sizes to suit different sizes of digits. As illustrated in FIG. 6C, in a preferred embodiment, an electrode, referred to herein as an active electrode 604, may be disposed on the digit on an infected region and the other electrode, alternatively referred to herein as a counter electrode 602, may be disposed on the digit on a non-infected region.

Figure 7A:
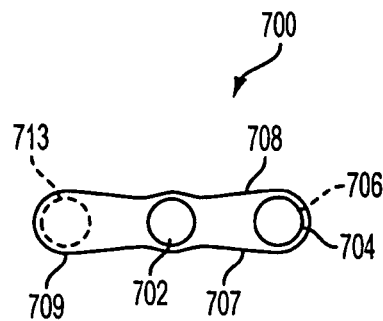
FIGS. 7A, 7B, and 7C illustrate an exemplary embodiment of a device in accordance with the invention.
Figure 7B:
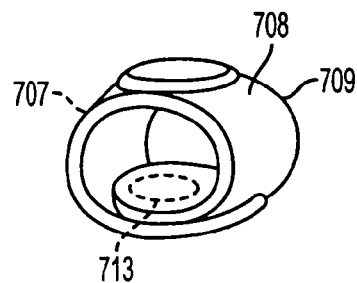
Figure 7C:
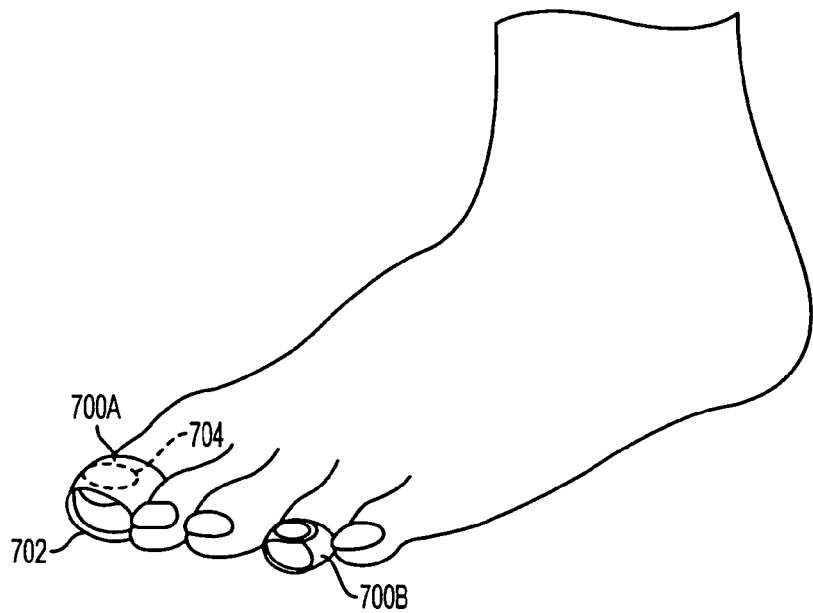

FIG. 7 illustrates an exemplary embodiment of a device in accordance with the invention. In the embodiment of FIG. 7A, a patch 700 comprises a base member 708 having a right lateral portion 707 and a left lateral portion 709. An adhesive 713 suitable for attaching the base member 708 to the skin of a patient, or alternatively suitable for attaching one portion of the base member 708 to another portion of the base member 708, may be deposited on either or both of the right lateral and left lateral portions 707, 709. A first electrode 702 may be positioned substantially midway between the left and right lateral portions 707, 709. A second electrode 704 may be positioned at a far end of either the right or left lateral portions 707, 709. In the embodiment of FIG. 7A, the second electrode 704 is illustrated as being positioned at the far end of the right lateral portion 707. A power source 706 may be interposed between the second electrode 704 and the base member 708. In alternate embodiments, the power source 706 may be placed at any location on the base member 708. FIG. 7B illustrates a configuration of the base member 708 suitable for use on a digit of a patient. In the illustration of FIG. 7B the left and right lateral portions 707, 709 are curvilinearly folded into a ring conformation. In the embodiment of FIG. 7B, the left and right lateral portions 707, 709 are overlapped, thus forming a ring conformation that completely surrounds the digit of a patient. The ring conformation is suitable for use on any digit because the left and right folded lateral portions 707, 709 together surround or substantially surround and embrace the digit. Adhesive 713 thereon substantially anchors one lateral portion to the other. The ring conformation thus formed may remain in place on the patient's digit by virtue of the physical embrace of the base member 708 around the digit, and/or by virtue of a composition (not shown) on one or both electrodes 702, 704, and/or by virtue of an adhesive (not shown) on the non-overlapped surfaces of the base member 708. Iontophoretic treatment, as described herein, may be pragmatically effected on portions of the digit by use of the patch 700. FIG. 7C illustrates two patches 700A and 700B embracing two separate digits of a patient. In the embodiment of FIG. 7C, a first patch 700A encircles a big toe of the patient. A second patch 700B encircles a fourth toe of the patient. As schematically illustrated in FIG. 7C, patches of the same conformation may be supplied in different sizes to suit different sizes of digits. As illustrated in FIG. 7C, in a preferred embodiment, an electrode, referred to herein as an active electrode 704, may be disposed on the digit on an infected region and the other electrode, alternatively referred to herein as a counter electrode 702, may be disposed on the digit on a non-infected region, which may optionally be underneath the toe.

Figure 8A:
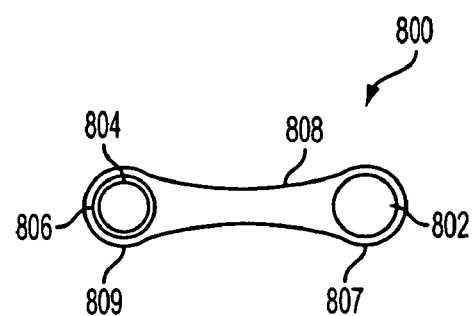
FIGS. 8A, 8B, and 8C illustrate an exemplary embodiment of a device in accordance with the invention.
Figure 8B:
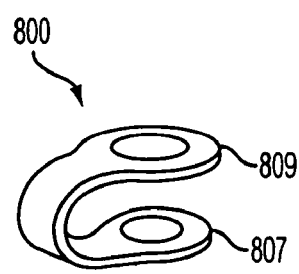
Figure 8C:
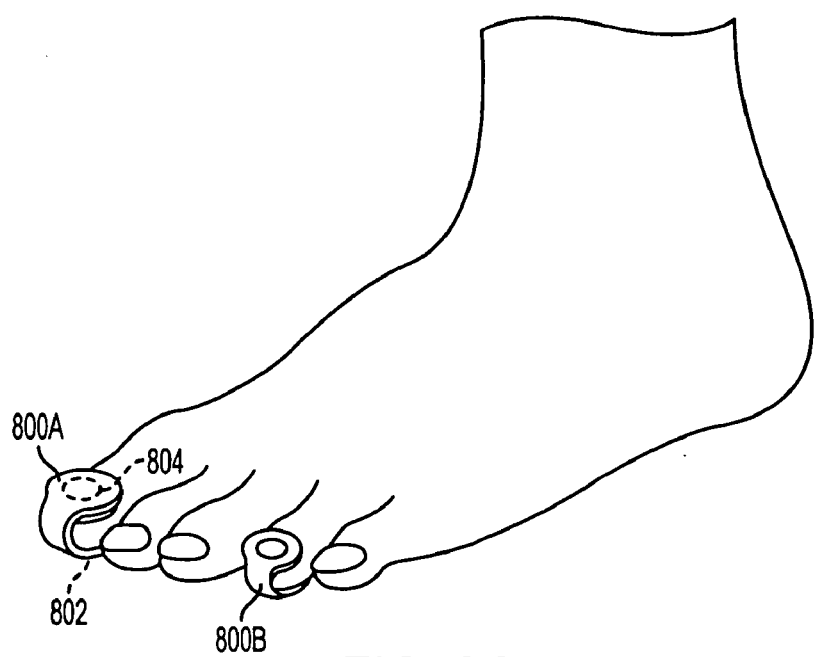

FIG. 8 illustrates an exemplary embodiment of a device in accordance with the invention. In the embodiment of FIG. 8A, a patch 800 comprises a base member 808 having a right lateral portion 807 and a left lateral portion 809. A first electrode 802 may be positioned at a far end of either the right or left lateral portions 807, 809. A second electrode 804 may be positioned at a far end of either the right or left lateral portions 807, 809. In the embodiment of FIG. 8A, the first electrode 802 is positioned at the far end of the left electrode 807; the second electrode 804 is illustrated as being positioned at the far end of the right lateral portion 809. A power source 806 may be interposed between the second electrode 804 and the base member 808. In alternate embodiments, the power source 806 may be placed at any location on the base member 808. FIG. 8B illustrates a configuration of the base member 808 suitable for use on a digit of a patient. In the illustration of FIG. 8B the left and right lateral portions 807, 809 are curvilinearly folded into a C-shaped conformation. The C-shaped conformation is suitable for use on any digit because the left and right folded lateral portions 807, 809 provide a base upon which the first and second electrodes 802, 804 may act together to embrace the digit. Iontophoretic treatment, as described herein, may be pragmatically effected on portions of the digit by use of the patch 800. FIG. 8C illustrates two patches 800A and 800B embracing two separate digits of a patient. In the embodiment of FIG. 8C, a first patch 800A embraces a big toe of the patient. A second patch 800B embraces a fourth toe of the patient. As schematically illustrated in FIG. 8C, patches of the same conformation may be supplied in different sizes to suit different sizes of digits. As illustrated in FIG. 8C, in a preferred embodiment, an electrode, referred to herein as an active electrode 804, may be disposed on the digit on an infected region and the other electrode, alternatively referred to herein as a counter electrode 802, may be disposed on the digit on a non-infected region.

Figure 9:
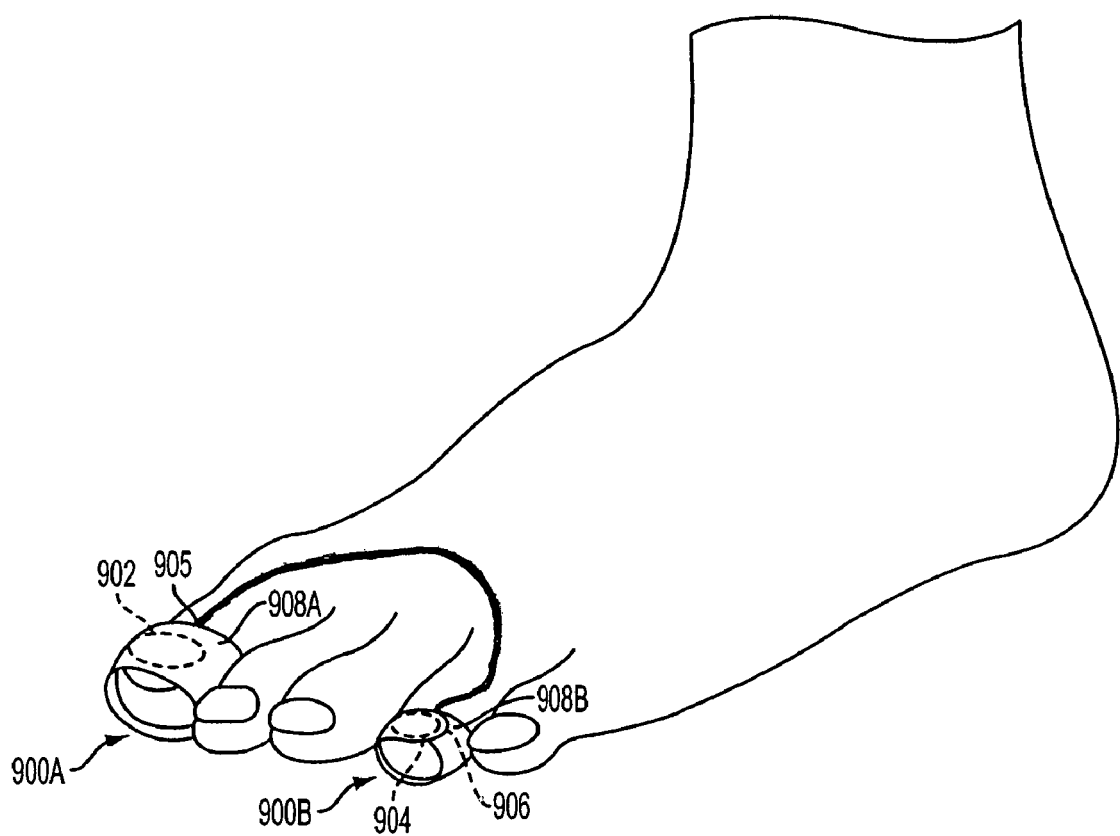
FIG. 9 illustrates an exemplary embodiment of a device in accordance with the invention.

FIG. 9 illustrates an exemplary embodiment of a device in accordance with the invention. In the embodiment of FIG. 9, a first patch 900A comprises a base member 908A. A second patch 900B comprises a base member 908B. A first electrode 902 may be positioned on the first patch 900A. A second electrode 904 may be positioned on the second patch 900B. A power source 906 may be interposed between the second electrode 904 and the base member 908B. In alternate embodiments, the power source 906 may be placed at any location on the base members 908A, 908B. An electrical conductor 905 may connect the power source to both the first and second electrodes 902, 904. The electrical conductor may take on any form known to those of skill in the art, such as, but not limited to, a flat ribbon or a cylindrical wire. In the illustration of FIG. 9, either the first patch 900A or the second patch 900B may include a composition including a compound to be administered to the patient. The patch including the compound may be referred to herein as the active patch; it may contain the active electrode. The remaining patch may include a counter electrode. The active electrode patch and the counter electrode patch are connected by conductive connection means, wherein the active patch is for application on an infected or diseased area of a first digit and the counter electrode on a different digit. Iontophoretic treatment, as described herein, may be pragmatically effected on portions of the digit by use of the patches 900A and 900B. Optionally, a device in accordance with the embodiment shown in FIG. 9 can be incorporated into a glove or sock with fingers for use on both the toes and fingers. Such a design may facilitate more facile application of such an embodiment.

It should be noted that, with respect to the use of the patch 500, 600, 700, 800, 900A and 900B, the active area of the patch, also referred to herein as the active electrode, may be applied on the nail alone, or on the nail, plus the surrounding skin area. In other words, the active electrode is preferably positioned over an infected or diseased area of the patient, while the counter electrode is preferably not positioned over the infected or diseased area of the patient. The positioning of the active electrode over the infected or diseased area of the patient and the counter electrode not over the infected or diseased area of the patient may assist in achieving maximum effect of the treatments described herein. It is also noted that the patches illustrated in FIGS. 5-9 may be used in a substantially flat plane, as on the surface of two adjacent portions of a patient's body. As illustrated schematically in FIGS. 3 and 4, the first and second electrodes may be positioned next to each other, and not above and below an infected or diseased area of a digit or other portion of a patients body. Optionally, patches 500, 600, 700, 800, 900A and 900B may be configured to attach to more than one digit, for example 2 or more adjacent infected digits. In such a way one patch can treat more than one digit. In addition, non-conductive adhesives useful for attaching the patch to a patients nail or skin surface may include a biocompatible permeable pressure sensitive adhesive such as Bio-PSA from Dow Corning. Other examples of biocompatible adhesives will be readily apparent to those of ordinary skill in the art.

Treatment

The term "treatment" as used herein encompasses any treatment of onychomycosis, and includes:

preventing the disease from occurring in a subject which may be predisposed to the disease but has not yet been diagnosed as having it;

inhibiting the disease, i.e., arresting its development; and/or relieving the disease, i.e., causing regression of the disease.

In the context of the present invention, relieving the disease, means attaining improvement in the subject's condition, including, but not limited to clinical improvement, microbiological improvement, and aesthetic improvement.

Treatment according to the present invention may include topical administration of a composition, the composition comprising an anti-fungal agent, in combination with the use of an electrically operated device to deliver the anti-fungal agent through the nail plate and onto the nail bed surface. Treatment may be of one time or multiple times; each time can be of several minutes to several hours. Treatment may be accomplished with the use of a kit, which may include the electrically operated device and the composition. Alternatively, treatment may be accomplished with a stand alone electrically operated device, which includes an anti-fungal composition.

Treatment may also be accomplished with the use of non-conventional drugs such as oxygen free radicals. Treatment may also include the use of electrode generated ions, such as, but not limited to, ions from a zinc electrode. Zinc ion treatment may be used as a separate treatment or as a supplementary treatment along with anti-fungi drugs. The zinc ions may play a secondary important role by boosting the local immune system against the fungus. Through the use of a device as described herein, both radicals and zinc ions may be generated locally and moved a short distance through the nail plate to the active site.

Furthermore, in an alternate embodiment, the use of urea and/or disulfide openers may allow for channel enlargement and may thus allow larger affective doses. Urea and/or disulfide openers disrupt the matrix (affecting the keratin network secondary structure and arrangement) to increase permeability.

In yet another embodiment, a device as described herein may be used, wherein the active composition includes antibacterial drugs and/or zinc ions for treatment of *Paronychia* (bacteria derived onychomycosis) of the nail, preventing fungal secondary-infections. It is noted that by using antibacterial drugs, the device described herein may be used to treat original/secondary bacterial infections. The active compounds may be antibiotics as well as zinc ions that can be generated in-situ on the nail plate. The antibiotics and active zinc ions (anti fungi and bacteria) can be delivered iontophoreticaly into the nail plate itself.

The Anti-Fungal Agent

Broadly, the anti-fungal agent may comprise an anti-fungal compound, or a pharmaceutically acceptable salt or derivative thereof. A single anti-fungal agent or mixture of such agents can be used and will be termed "anti-fungal agent" or "anti-fungal compound" herein, interchangeably.

There is no particular limitation on the anti-fungal agents used in the compositions of this invention, as long as they possess a certain degree of water solubility, which is attained by (1) being ionic; (2) being polar, as indicated by a partitioning coefficient between water and Octane which is greater than about 0.5; or (3) being solubilized in any way, known to those skilled in the art of pharmaceutical formulation, including as example, but not limited to, incorporation in nanoparticles, liposomes, microemulsions.

By way of example, preferred suitable anti-fungal agents may be comprised of polyenes, e.g., Natamycin, Nystatin; allylamines, e.g., Naftifine, Terbinafine; imidazoles, e.g., Bifonazole, Chlotrimazole, Econazole, Fenticonazole, Ketocanazole, Miconazole, Oxiconazole; triazoles, e.g., Fluconazole, Itraconazole, Terconazole, tolnaftate, ciclopirox, undecylenic acid, sulbentine; and morpholines, e.g., amorolfine, and the related morpholines.

Oxidizing agents may be used in combination with other anti-fungal agents. Such oxidizing agents may be incorporated into a kit or device of the present invention, or produced in-situ by an electrochemical process.

The amount of the anti-fungal agent present in the composition, as described hereinbelow, may be an amount that is therapeutically effective, i.e. the amount that will result in an effective treatment of the onychomycosis when applied in accordance with the instructions described herein.

The amount of the active anti-fungal agent in the composition will depend on such factors as its polarity, structure, anti-fungal activity, penetration rate via electromotive forces, diffusion characteristics, and penetration behavior in the nail. Generally, the amount of the active anti-fungal agent in the composition may be any amount effective to kill the infecting microorganism, which will generally be greater than the Mean Inhibitory Concentration (MIC).

The therapeutically effective amount may vary depending on the subject and the severity of the affliction and may be determined routinely by one of ordinary skill in the art in light of the teaching herein.

Generally, a therapeutically effective amount will be from about one-half percent by weight (0.05%) to about fifteen percent by weight (15%) based on the total final weight of the composition. Preferably, the amount will be about 0.1% to about 10% by weight and more preferably about 0.2% to about 8% by weight. The amount present in the composition will be dependent in part on the length of the treatment, as discussed hereinafter.

The Composition

Broadly, the composition comprises a therapeutically effective amount of an anti-fungal compound, or a pharmaceutically acceptable salt thereof, or mixture of such agents and at least one pharmaceutically acceptable excipient to provide a mixture having a consistency to be administered to the surface of a nail together with an iontophoretic patch, so that the anti-fungal agent is delivered into and through the nail plate. Generally the composition is a liquid or semisolid, such as a cream, ointment, lotion, gel, or hydrogel having a solvent in which the anti-fungal compound, or its salt or derivative, is dissolved. In one preferred embodiment, the composition is a gel, having conductive properties, as well as adhesion properties. Yet, in a further preferred embodiment, the gel is a hydrogel, having conductive properties, as well as adhesion properties.

Thus, in one embodiment the composition may contain at least the anti-fungal compound, a solvent for the compound, and a gelling agent. Preferably, the composition is water-based, which means that the solvent is preferably water-miscible. It is important that the composition is electrically conductive. In addition, the composition may include a surfactant to aid in the delivery of the anti-fungal into and through the nail plate; a keratolytic agent to aid in the loosening, disintegration, or decomposition of a thickened nail plate; a film-forming agent; a buffering agent to adjust the pH of the composition; and/or an adherence-promoting agent to assist in adhering the composition to the nail plate.

Preferable excipients are such that cause enhancement of the electrical current, thereby improving the delivery of anti-fungal agents into and through the nail plate.

Typically, amounts of anti-fungal agent in the range of from about 0.5 to 20 percent by weight, preferably from about 1 to 10 percent, by weight, of the total will suffice for compositions for treatment as well as compositions for prevention.

The composition may be applied directly to the nail or applied in an absorbent pad. It can also be incorporated as an integral part of the iontophoretic device.

Figure 10:
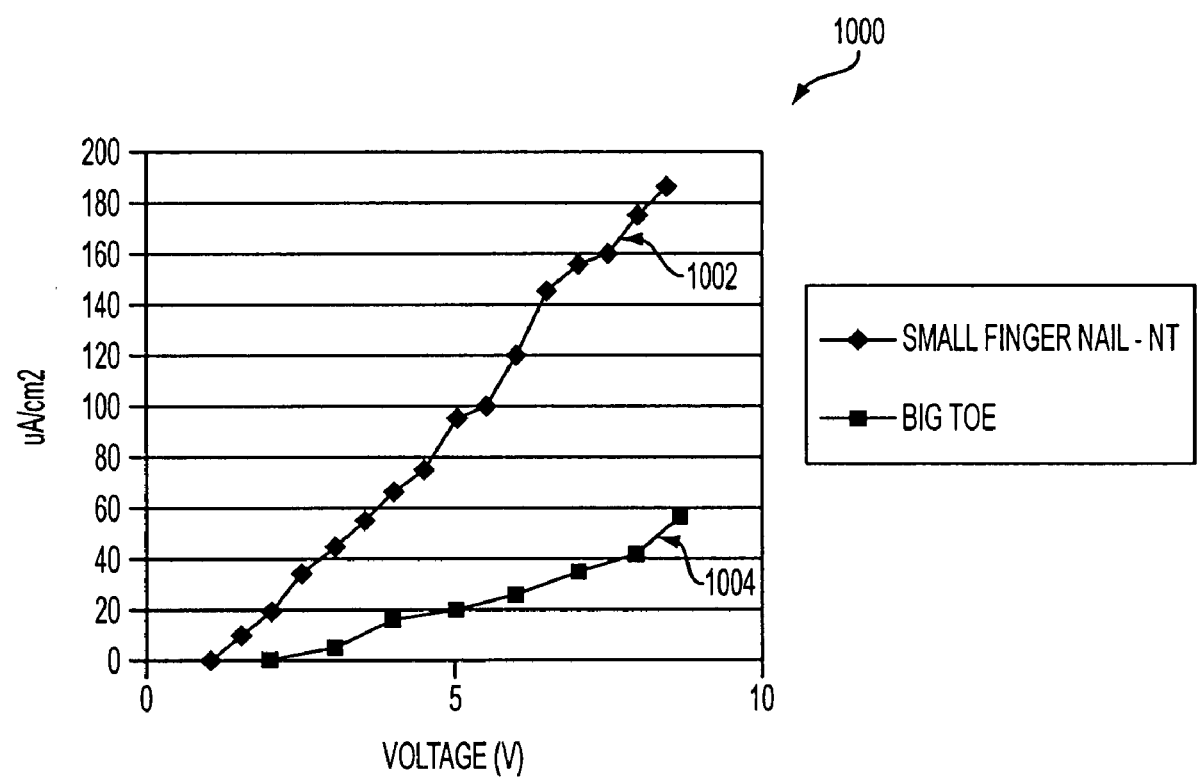
FIG. 10 is a graph of current density versus voltage as a function of nail type for a circuit formed by a human finger or toe in series with the electrodes of an iontophoretic device, in accordance with an embodiment of the invention.

Experimental Result of Electrical Current Passed through Nails Using an Iontophoretic Device FIG. 10 is a graph 1000 of current density versus voltage as a function of nail type for a circuit formed by a human finger or toe in series with the electrodes of an iontophoretic device, in accordance with an embodiment of the invention. Nail types comprised of fingernails 1002 and toenails 1004 are illustrated. The graph was generated from experiments performed in-vivo in human volunteers. The results demonstrate that an iontophoretic device, as described above, can deliver iontophoretically-significant electrical currents. The current—voltage relationship is linear, and an electrical current density of more than 5 uA/cm$^2$ is attained in low voltage devices. The electrical current can be further enhanced using various agents, which elevate nail conductivity and consequently, the delivery of anti-fungal agents into and through the nail plate.

Additional Experimental Results

The purpose of the experiment described hereinbelow was to study the electrical current that can be delivered through nail when voltage in the range of 1.5-9V is applied. A further objective was to make an assessment of the ability to enhance current using a known nail moisturizing agent—urea.

From the study, the following observations and conclusions could be made:

The nail conducts current in the range of 7-20 uAmp under the anode.

Such current, exerted for 20 minutes to several hours is expected to deliver cationic active agents into and through the nail.

The anode transmits a higher currents voltage than the cathode. The anode should preferably be placed on the nail. (Note that candidate onychomycosis drugs, e.g., ciclopirox and terbinafine, are cations and will be delivered under the anode.)

Increase in currents voltage will increase the potentials that will be recorded on the nail bed and will increase the iontophoresis effect.

A Urea gel seems to improve the currents values after 30 minutes.

Experiment Materials:
Study material: Onychomycosis patch, with regular Gel or with urea Gel and an auxiliary power supply.

Patches: Experimental patches, including separate anode and cathode, both including Ag/AgCl and coated by hydrogen. Each patch was designed to be 1 cm$^2$.

Gel: Two types of gel were used, (1) "Regular gel", base on water, 2% Natrosol and 2% NaCl, and (2) "Urea Gel", comprising 20% urea in a regular gel.

Study subject: 13 Healthy subjects, aged 30-60.

Duration of Treatment: Single use for 30 minutes on each thumb nail bed.

Study Design:
Group 1: Onychomycosis patch with Regular Gel was applied to the thumb nail bed with a constant voltage of 3 Volt. The current was followed up during 30 minutes treatment period. Currents measurements were recorded during the experiment at initial point, 15 minutes and 30 minutes after the beginning. Five subjects were enrolled on this group. On each subject the Anode was applied to the nail bed of one leg, the cathode was applied to the nail bed of the other leg.

Group 2: Onychomycosis patch with Urea Gel was applied to the thumb nail bed with a constant voltage of 3 Volt. The current was followed up during 30 minutes treatment period. Currents measurements were recorded during the experiment at initial point, 15 minutes and 30 minutes after the beginning. Four subjects were enrolled on this group. On each subject the Anode was applied to the nail bed of one leg. The cathode was applied to the nail bed of the other leg.

Group 3: Onychomycosis patch with Regular Gel was applied to thumb nail bed of the left leg. The Onychomycosis patch with Urea Gel was applied to thumb nail bed of the right leg. In this group only anodes were applied to nail bed on both gel types. Currents measurements were recorded immediately following application. The voltage was adjusted to the following values: 1.5V, 3V, 4.5V, 6V, 7.5V and 9V. At the same Voltage values records also were taken after 30 minutes. Four subjects were enrolled in this group.

All variable assessments were followed up before, during & after each one of the treatments.

Figure 11:
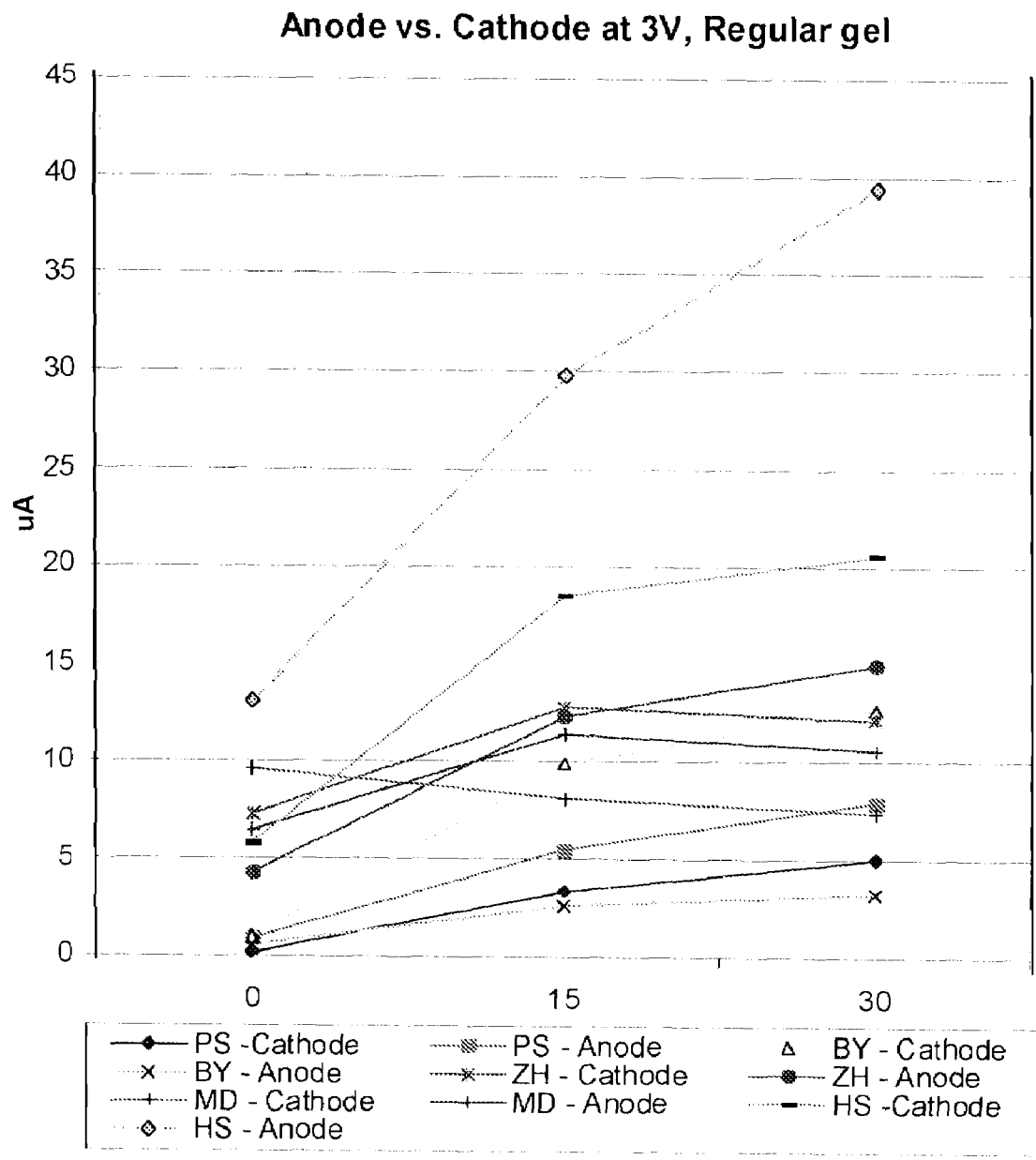
FIG. 11 is a graph of experimental results showing current over time for an onychomycosis patch with regular gel.

Experiment Results:
Group 1: Regular gel—currents potential differences between anode and cathode were measured as shown in FIG. 11. The anode currents potentials varies between 0.59-13.1 µA at 0 minutes and 3.26-39.4 µA after 30 minutes. The cathode currents potentials varies between 0.2-9.6 µA at 0 minutes and 5-20.57 µA after 30 minutes. Four cases out of five (80%) the anode transferred a higher currents voltage.

Group 2: Urea gel—currents potential differences between anode and cathode were measured. The anode currents potentials varies between 0.1-4.2 µA at 0 minutes and 0.25-19.6 µA after 30 minutes. The cathode currents potentials varies between 0.2-3.3 µA at 0 minutes and 0.6-10 µA after 30 minutes. Three cases out of four (75%) the anode transferred a higher currents voltage.

Figure 12:
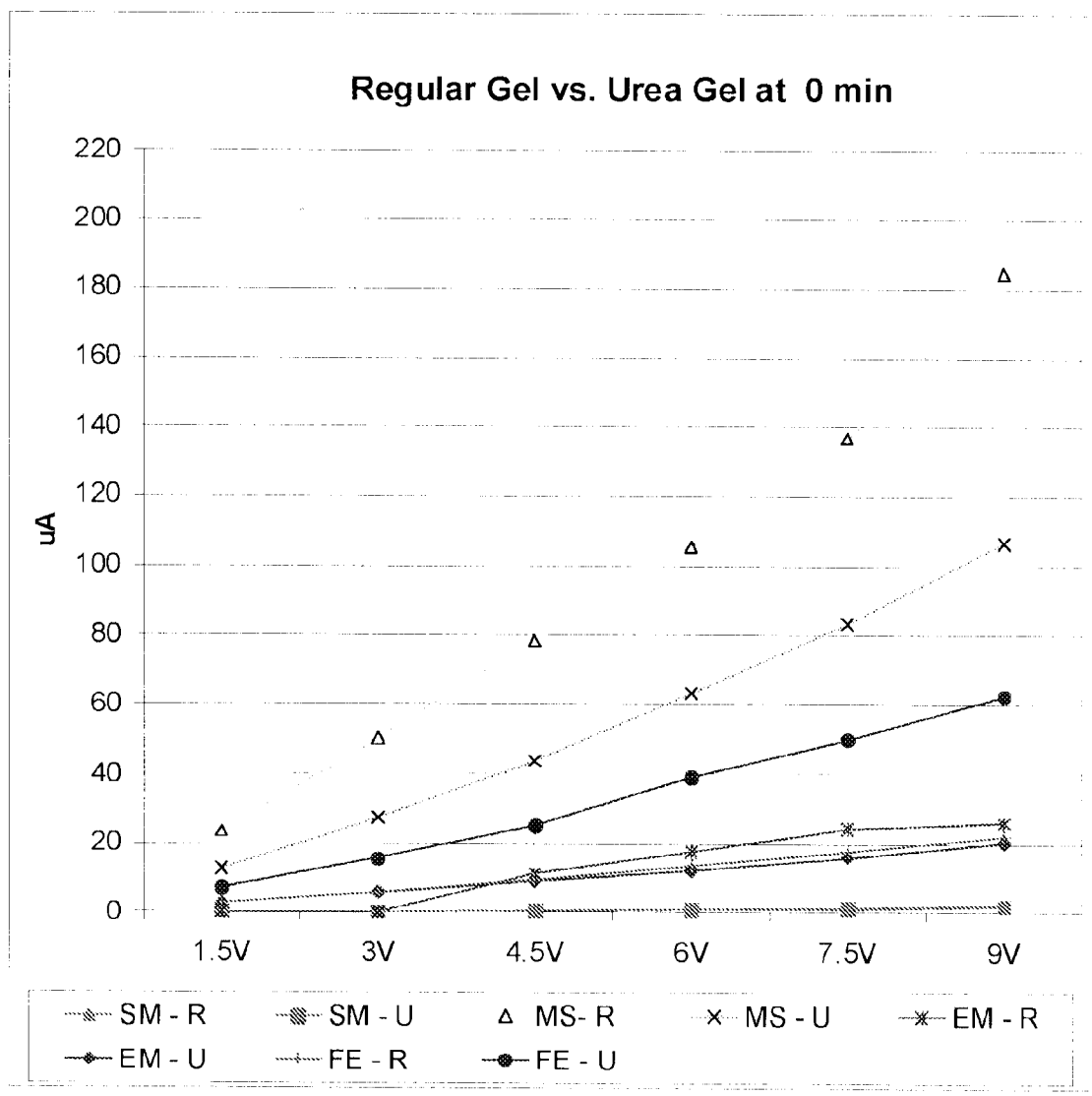
FIG. 12 is a graph of experimental results showing a comparison between regular gel and urea gel at 0 minutes and FIG. 13 is a graph of experimental results showing a comparasion between regular gel and urea gel at 30 minutes.

Group 3: Comparison between Regular vs. Urea Gels on the same subject. The different currents potential at 0 minutes and 30 minutes. The following table and FIG. 12 demonstrate the currents measurements recorded after 0 minutes:

|  |  | 1.5 V | 3 V | 4.5 V | 6 V | 7.5 V | 9 V |  |
|---|---|---|---|---|---|---|---|---|
| Anode | 0% Urea | 0.2 | 0.27 | 0.52 | 0.86 | 1.23 | 1.83 | SM |
| Anode | 20% Urea | 0.2 | 0.3 | 0.6 | 1 | 1.5 | 2.3 | SM |
| Anode | 0% Urea | 23.6 | 50.4 | 78.4 | 105.5 | 136.7 | 184.4 | MS |
| Anode | 20% Urea | 12.74 | 27.4 | 43.7 | 63.18 | 83.44 | 106.68 | MS |
| Anode | 0% Urea | 0.1 | 0.2 | 11.2 | 17.7 | 24.2 | 25.9 | EM |
| Anode | 20% Urea | 2.87 | 6.14 | 9.23 | 12.33 | 15.97 | 20.27 | EM |
| Anode | 0% Urea | 2.83 | 6.2 | 9.78 | 13.59 | 17.86 | 22.19 | FE |
| Anode | 20% Urea | 7.3 | 15.7 | 25.3 | 39.1 | 50 | 62.4 | FE |

At 0 minutes the conductivity of the Regular gel was higher significantly in 2 cases out of 4 (50%) compared to the Urea gel.

Figure 13:
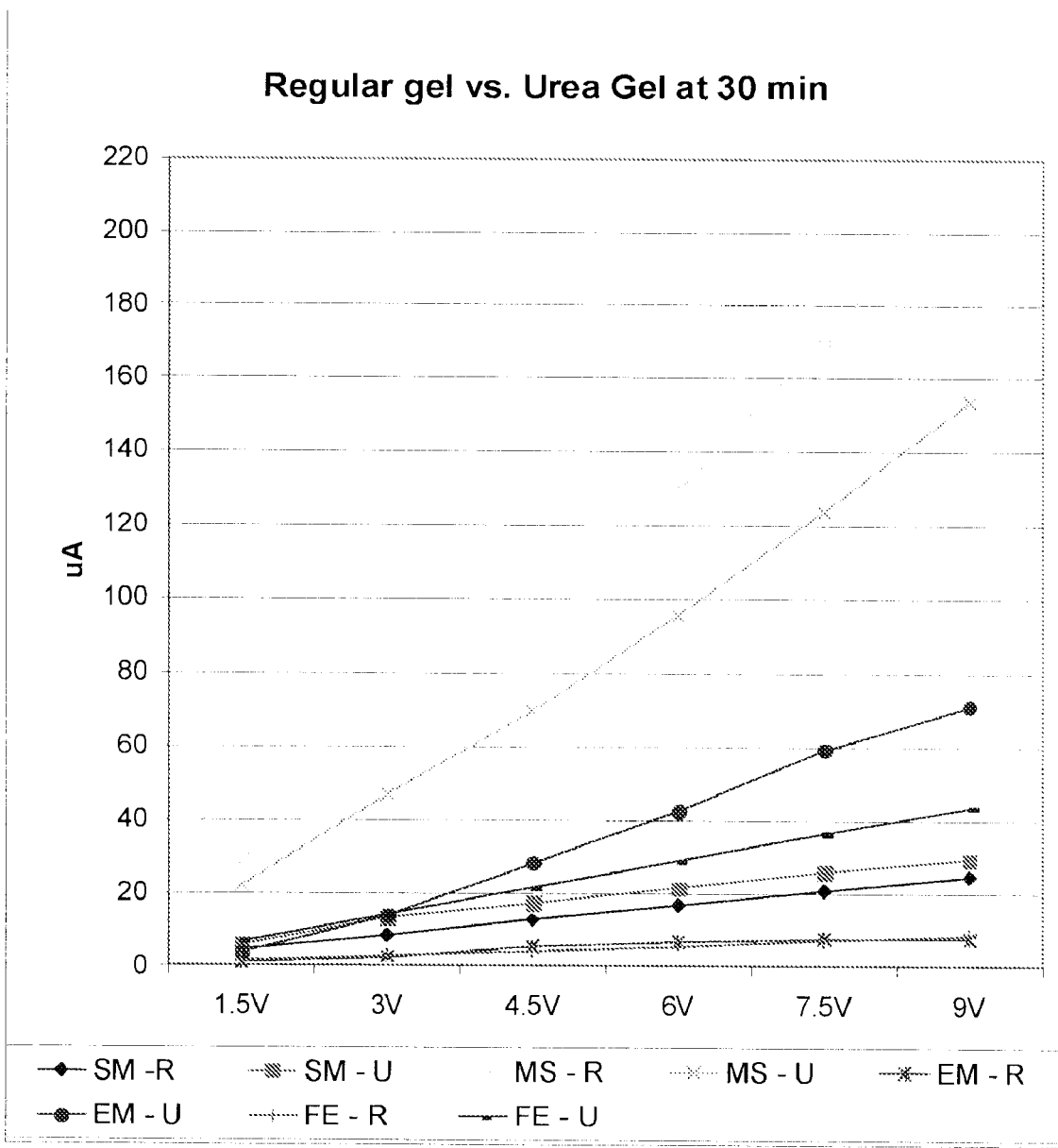

The following table and FIG. 13 demonstrate the currents measurements recorded after 30 minutes:

|  |  | 1.5 V | 3 V | 4.5 V | 6 V | 7.5 V | 9 V |  |
|---|---|---|---|---|---|---|---|---|
| Anode | 0% Urea | 4.52 | 8.33 | 12.69 | 16.8 | 20.77 | 24.62 | SM |
| Anode | 20% Urea | 6.1 | 13.1 | 17.2 | 21.3 | 25.8 | 29.2 | SM |
| Anode | 0% Urea | 28.9 | 62.1 | 93.9 | 129.4 | 171.1 | 211.5 | MS |
| Anode | 20% Urea | 21.78 | 46.95 | 69.71 | 95.46 | 123.91 | 153.78 | MS |
| Anode | 0% Urea | 1 | 2.5 | 5.5 | 6.7 | 7.5 | 7.7 | EM |
| Anode | 20% Urea | 3.72 | 13.8 | 28.3 | 42.45 | 59.11 | 70.9 | EM |
| Anode | 0% Urea | 1.4 | 2.81 | 4.21 | 5.58 | 6.98 | 8.58 | FE |
| Anode | 20% Urea | 6.8 | 14.1 | 21.3 | 28.8 | 36.3 | 43.4 | FE |

At 30 minutes the conductivity of the Urea gel was higher significantly in 3 cases out of 4 (75%) compared to the Regular gel.

Anode—Cathode Analysis

Figure 14:
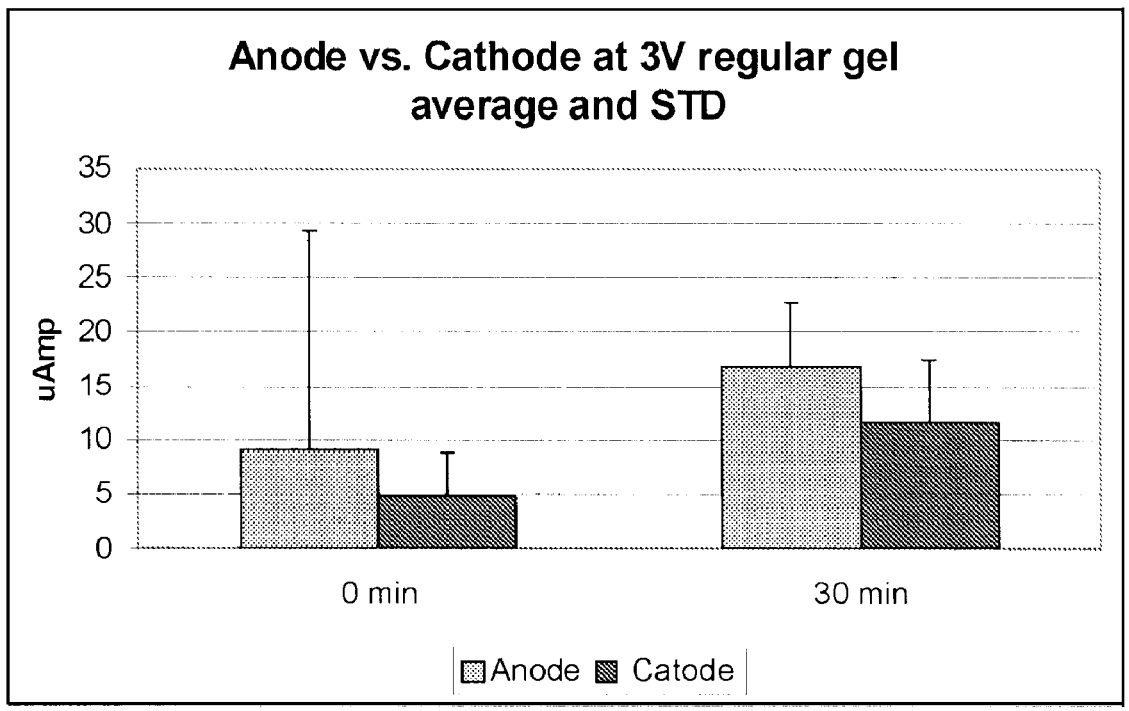
FIGS. 14 and 15 show the average currents at 0 minutes and 30 minutes for the regular gel and the urea gel, respectively.

On the regular gel, as can be seen in FIG. 14: The Average currents recorded on the Anode at 0 minutes were 9.16 µA with STD of 16.03 µA. The Average currents recorded on the Cathode at 0 minutes were 4.79 µA with STD of 4.06 µA. The Average currents recorded on the Anode at 30 minutes were 16.87 µA with STD of 20.23 µA. The Average currents recorded on the Cathode at 30 minutes were 11.57 µA with STD of 5.98 µA.

Figure 15:
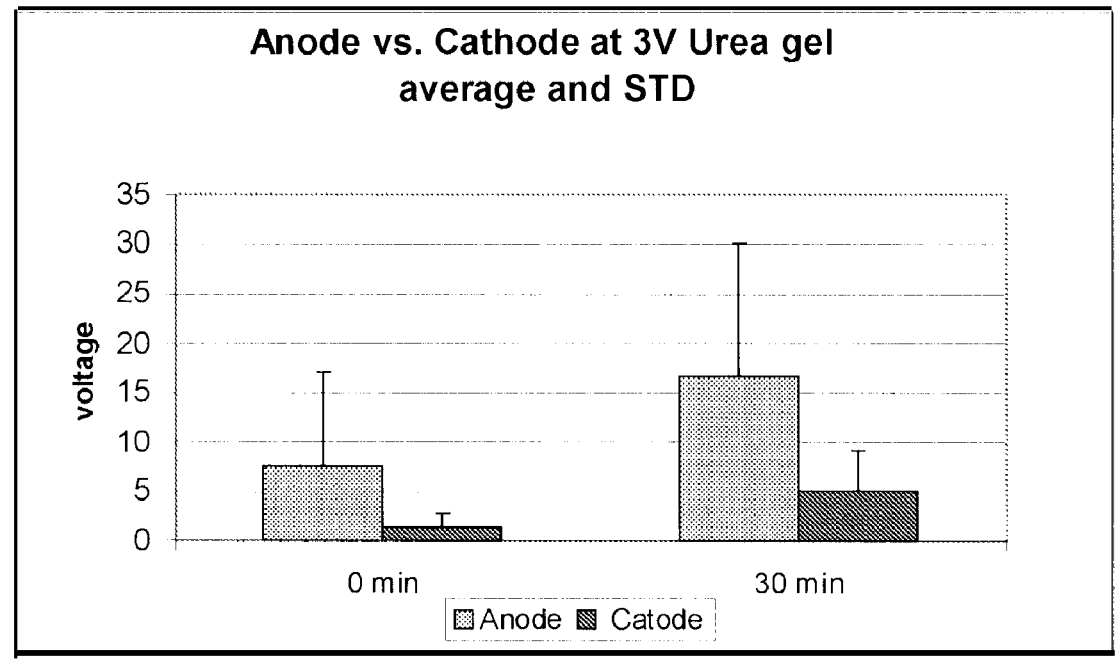

On the Urea gel, as can be seen in FIG. 15: The Average currents recorded on the Anode at 0 minutes were 7.63 µA with STD of 9.36 µA. The Average currents recorded on the Cathode at 0 minutes were 1.56 µA with STD of 1.31 µA. The Average currents recorded on the Anode at 30 minutes were 16.64 µA with STD of 13.49 µA. The Average currents recorded on the Cathode at 30 minutes were 5.2 µA with STD of 4.03 µA.

No side effects or adverse effects were noted.

EXPERIMENT CONCLUSIONS

The nail conducts current in the range of 7-20 uAmp under the anode.

Such current, exerted for 20 minutes to several hours is expected to deliver cationic active agents into and through the nail.

The anode transmits a higher currents voltage than the cathode. The anode should be placed on the nail. (Note that candidate onychomycosis drugs, e.g., ciclopirox and terbinafine, are cations and will be delivered under the anode.)

Increase in currents voltage will increase the potentials that will be recorded on the nail bed and will increase the iontophoresis effect.

The Urea gel seems to improve the currents values after 30 minutes.

Those skilled in the art can appreciate from the foregoing description that the broad techniques of the embodiments of the present invention can be implemented in a variety of forms. Therefore, while the embodiments of this invention have been described in connection with particular examples thereof, the true scope of the embodiments of the invention should not be so limited since other modifications will become apparent to the skilled practitioner upon a study of the drawings, specification, and following claims.

What is claimed is:

1. A method of treating onychomycosis, the method comprising:
    applying a device to at least one digit for the treatment of onychomycosis, the device comprising:
        at least one active electrode for facilitating delivery of an anti-fungal agent into an onychomycosis infected region of the at least one digit, by application of an electrical current to the region;
        at least one counter electrode facilitating closing of an electrical circuit with the at least one active electrode; and
        at least one power source for providing a current and voltage, connected through a conductive media to the active electrode and the counter electrode;
    disposing the at least one active electrode on the onychomycosis infected region of the at least one digit; and
    disposing the at least one counter electrode on a non-infected region of the at least one digit.

2. The method of claim 1, wherein the device further comprises
    at least one base member supporting the at least one active electrode, the at least one counter electrode, and the at least one power source,
    wherein the device has a first flat position and a second curved position conforming to the curvature of the digit, and
    wherein the at least one active electrode is adapted to be disposed on the onychomycosis infected region of the at least one digit and the at least one counter electrode is adapted to be disposed on a non-infected region of the at least one digit in both the first position and the second position.

3. The method of claim 2, wherein the at least one active electrode, the at least one power source, and the at least one counter electrode are made by a printing technique.

4. The method of claim 3, wherein the at least one active electrode, the at least one power source, and the at least one counter electrode are printed on the base member.

5. The method of claim 2, wherein the at least one power source is integrally formed with the at least one active electrode.

6. The method of claim 2, further comprising a composition, wherein the composition comprises at least one anti-fungal agent.

7. The method of claim 6, wherein the at least one anti-fungal agent is selected from the group consisting of: polyenes; allylamines; imidazoles; triazoles; and morpholines, Natamycin, Nystatin, Naftifine, Terbinafine, Bifonazole, Chlotrimazole, Econazole, Fenticonazole, Ketocanazole, Miconazole, Oxiconazole, Fluconazole, Itraconazole, Terconazole, tolnaftate, ciclopirox, undecylenic acid, sulbentine, amorolfine, and related morpholines, oxidizing agents, zinc ions, antibiotics and combinations thereof.

8. The method of claim 6, wherein the at least one anti-fungal agent comprises terbinafine.

9. The method of claim 6, wherein the composition further comprises a conductive interfacing material.

10. The method claim 9, wherein the conductive interfacing material is a hydrogel.

11. The method of claim 6, wherein the composition comprises at least one pharmaceutically acceptable excipient that cause enhancement of an electrical current into and through human nail and/or skin.

12. The method of claim 6, wherein the composition further comprises at least one of a surfactant and a keratolytic agent.

13. The method of claim 6, wherein the composition further comprises a water miscible solvent and a gelling agent.

14. The method of claim 6, wherein the composition is at least one of a cream, ointment, lotion, gel, and hydrogel.

15. The method of claim 6, wherein the device promotes delivery of the anti-fungal agent by at least one of iontophoresis, electrotransportation, electroosmosis, and electroporation.

16. The method of claim 2, wherein the voltage or current are fixed.

17. The method of claim 2, wherein the at least one active electrode and the at least one counter electrode lie in a first plane in the first position and lie in a second plane in the second position, and the first plane and the second plane are substantially co-planar.

18. The method of claim 2, wherein the number of the at least one active electrode and the number of the at least one counter electrode is unequal.

19. The method of claim 2, wherein the at least one base member is one base member.

20. The method of claim 2, wherein the at least one active electrode and the at least one counter electrode are on the same side of the at least one digit when in both the first position and the second position.

21. The method of claim 1, wherein the at least one power source is a thin and flexible power source.

22. The method of claim 21, wherein the power source is an open liquid state electrochemical cell comprising: a first layer of insoluble negative pole; a second layer of insoluble positive pole; and a third layer of aqueous electrolyte being disposed between the first and second layers and comprising: a deliquescent material for keeping the open cell wet at all times; an electroactive soluble material for obtaining a predetermined ionic conductivity; and a water-soluble polymer for obtaining a required viscosity for adhering the first and second layers to the third layer.

23. The method of claim 1, further comprising electronics to control the current.

24. The method of claim 1, wherein the counter electrode is disposed on a non-infected region of the at least one digit that is on the opposite side of the at least one digit from the infected region.

25. The method of claim 1, wherein the device further comprises a base member having left and right lateral portions and a midline portion, and the method further comprises curvilinearly folding the left and right lateral portions on the at least one digit.

26. The method of claim 1, wherein the at least one active electrode is an anode.

27. The method of claim 1, wherein the at least one active electrode is at least one anode and the at least one counter electrode is at least one cathode, and the method further comprises disposing the at least one anode on the onychomycosis infected region of the at least one digit and the at least one cathode on a non-infected region of the at least one digit, to achieve maximal treatment effect of onychomycosis.

28. The method of claim 1, wherein the device is incorporated into a glove or sock.

29. The method of claim 1, wherein the at least one active electrode and/or the at least one counter electrode is a plurality of electrodes.

30. The method of claim 1, wherein the number of the at least one active electrode and the number of the at least one counter electrode is unequal.

31. The method of claim 1, wherein the device further comprises
at least one base member supporting the at least one active electrode, the at least one counter electrode, and the at least one power source,
wherein the device has a first flat position and a second curved position conforming to the curvature of the digit and wherein the at least one active electrode and the at least one counter electrode are spaced within about 5mm to about 10 mm of each other in both the first position and the second position.

32. The method of claim 1, wherein the device further comprises
at least one base member supporting the at least one active electrode, the at least one counter electrode, and the at least one power source, and
at least one anti-fungal agent that is a terbinafine compound in a formulation, wherein the formulation is electrically conductive and comprises the terbinafine compound solubilized in water, terbinafine cations and a gelling agent.

33. The method of claim 1, wherein the device farther comprises a device for the treatment of onychomycosis comprising at least one flexible wearable patch conformable to the contour of at least a non-nail portion of at least one digit and at least part of the nail portion of the at least one digit, the flexible wearable patch comprising:
a composition disposed on the at least one active electrode; and
a base member supporting the at least one active electrode, the at least one counter electrode, and the at least one power source, wherein the base member is in a folded configuration on the digit.

34. The method of claim 1, wherein the counter electrode is not disposed on an infected region of the at least one digit.

35. The method of claim 1, further comprising applying an anti-fungal agent to a nail of the at least one digit and/or to the device.

36. The method of claim 1, wherein the device further comprises an anti-fungal agent.

37. The method of claim 1, further comprising removing the device and re-applying the device multiple times.

38. The method of claim 1, further comprising delivering an anti-fungal agent by at least one of iontophoresis, electrotransportation, electroosmosis, and electroporation.

39. The method of claim 1, wherein the device further comprises
- at least one base member comprising a midline portion, a left lateral portion and a right lateral portion, wherein the at least one base member supports the at least one active electrode, the at least one counter electrode, and the at least one power source,
- wherein the at least one active electrode is supported on the midline portion, and
- wherein the at least one active electrode is adapted to be disposed on the onychomycosis infected region of the at least one digit, the at least one counter electrode is adapted to be disposed on a non-infected region of the at least one digit, and the left lateral portion and the right lateral portion are adapted to wrap around the at least one digit.

40. The method of claim 39, wherein the at least one counter electrode are supported on the midline portion of the at least one base member.

* * * * *

UNITED STATES PATENT AND TRADEMARK OFFICE
CERTIFICATE OF CORRECTION

PATENT NO.      : 7,647,100 B2                                    Page 1 of 1
APPLICATION NO. : 10/890297
DATED           : January 12, 2010
INVENTOR(S)     : Nitzan et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1514 days.

Signed and Sealed this

Sixteenth Day of November, 2010

David J. Kappos
*Director of the United States Patent and Trademark Office*